(12) United States Patent
Ujihara et al.

(10) Patent No.: US 9,567,616 B2
(45) Date of Patent: Feb. 14, 2017

(54) PROCESS FOR PRODUCING TARGET SUBSTANCE BY FERMENTATION

(75) Inventors: Tetsuro Ujihara, Ibaraki (JP); Tetsuya Abe, Yamaguchi (JP); Makoto Yagasaki, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 13/983,917

(22) PCT Filed: Feb. 9, 2012

(86) PCT No.: PCT/JP2012/052947
§ 371 (c)(1),
(2), (4) Date: Aug. 6, 2013

(87) PCT Pub. No.: WO2012/108493
PCT Pub. Date: Aug. 16, 2012

(65) Prior Publication Data
US 2013/0323784 A1    Dec. 5, 2013

(30) Foreign Application Priority Data
Feb. 9, 2011  (JP) ................. 2011-025750

(51) Int. Cl.
| C12P 13/10 | (2006.01) |
| C12P 13/04 | (2006.01) |
| C12P 13/08 | (2006.01) |
| C12N 1/20  | (2006.01) |
| C12N 9/12  | (2006.01) |

(52) U.S. Cl.
CPC ............... *C12P 13/10* (2013.01); *C12N 1/20* (2013.01); *C12N 9/1205* (2013.01); *C12P 13/04* (2013.01); *C12P 13/08* (2013.01); *C12Y 207/01069* (2013.01); *C12Y 207/03009* (2013.01); *Y02P 20/52* (2015.11)

(58) Field of Classification Search
None
See application file for complete search history.

(56) References Cited

U.S. PATENT DOCUMENTS

| 6,921,651 B2 | 7/2005 | Farwick et al. | |
| 2003/0092137 A1* | 5/2003 | Farwick et al. | 435/106 |
| 2009/0081740 A1* | 3/2009 | Binder et al. | 435/115 |
| 2009/0142843 A1 | 6/2009 | Cervin et al. | |

FOREIGN PATENT DOCUMENTS

| EP | 2 330 184 | 6/2011 |
| JP | 05-049441 | 3/1993 |
| JP | 2010-539941 | 12/2010 |
| WO | 02/074944 | 9/2002 |
| WO | 03/004670 | 1/2003 |
| WO | 03/004674 | 1/2003 |
| WO | 2009/042878 | 4/2009 |

OTHER PUBLICATIONS

Jahreis, et al., "Ins and outs of glucose transport systems in eubacteria", FEMS Microbiol. Rev., vol. 32 (2008) 891-907.
Kornberg, "If at first you don't succeed . . . fructose utilization by *Escherichia coli*", Advan. Enzyme Regul., vol. 42 (2002) 349-60.
Moon, et al., "Analyses of enzyme II gene mutants for sugar transport and heterologous expression of fructokinase gene in Corynebacterium glutamicum ATCC 13032", FEMS Microbiol. Letters, vol. 244 (2005) 259-66.
Postma, et al., "Phosphoenolpyruvate: Carbonhydrate Phosphotransferase Systems of Bacteria", Microbiol. Reviews, vol. 57, No. 3 (1993) 543-94.
Saier, "Families of transmembrane sugar transport proteins", Molecular Microbiology, vol. 35, No. 4 (2000) 699-710.
Saier, et al., "Proposed Uniform Nomenclature for the Proteins and Protein Domains of the Bacterial Phosphoenolpuruvate:Sugar Phosphotransferase System", J. Bacteriology, vol. 174, No. 5 (1992) 1433-38.
Saier, et al., "Evolution of the bacterial phosphotransferase system: from carriers and enzymes to group translocators", Biochemical Society Transactions, vol. 33, Part 1 (2005) 220-24.
Dominguez, et al., "Carbon-flux distribution in the central metabolic pathways of Corynebacterium glutamicum during growth on fructose", Eur. J. Biochem., vol. 254 (1998) 96-102.
Moon, et al., "The Phosphotransferase System of Corynebacterium glutamicum: Features of Sugar Transport and Carbon Regulation", J. Mol Microbiol Biotechnol., vol. 12 (2007) 43-50.
Tanaka, et al., "Regulation of the expression of phosphoenolpyruvate: carbohydrate phosphotransferase system (PTS) genes in Corynebacterium glutamicum R", Microbiology, vol. 154, No. Pt 1 (2008) 264-74.
Georgi, et al., "Lysine and glutamate production by Corynebacterium glutamicum on glucose, fructose and sucrose: Roles of malic enzyme and fructose-1,6-bisphosphatase", Metabolic Engineering, vol. 7 (2005) 291-301.

* cited by examiner

*Primary Examiner* — Mindy G Brown
(74) *Attorney, Agent, or Firm* — Fitzpatrick, Cella, Harper & Scinto

(57) ABSTRACT

A target substance can be efficiently produced by culturing, in a medium, a coryneform bacterium in which the activity of a PTS protein relating to fructose uptake is reduced or lost as compared with a parent strain and the bacterium can produce the target substance, allowing the target substance to form and accumulate in a culture; and collecting the target substance from the culture.

8 Claims, No Drawings ically take up fructose and converts it into fructose 1-phosphate as well as FruK (PfkB)
PROCESS FOR PRODUCING TARGET SUBSTANCE BY FERMENTATION This application is a National Phase of PCT Application No. PCT/JP2012/052947 filed Feb. 9, 2012, which in turn claims benefit of Japanese Application No. 2011-025750 filed Feb. 9, 2011.

TECHNICAL FIELD

The present invention relates to a process for producing a target substance using a coryneform bacterium, in which the activity of a PTS protein relating to fructose uptake has been reduced or lost as compared with a parent strain, and which can produce the target substance.

BACKGROUND ART

One of the methods for improving the productivity in a method for producing a target substance by a fermentation process includes a method for modifying the ability of uptake of a sugar which is a starting material.

A research on the mechanisms of uptake of a carbohydrate such as a sugar by a microorganism has been advanced, and the mechanisms are known to be classified into several types. These include, in particular, a phosphoenolpyruvate: sugar phosphotransferase system (hereinafter also referred to as PTS or phosphotransferase system), which is a transporter which phosphorylate and thereby take up a major sugar (Non-Patent Document 1).

The PTS system is composed of a substrate-independent common system EI (encoded by ptsI), HPr (encoded by ptsH), and a substrate-specific component EII (Non-Patent Documents 2 to 4).

The substrate-specific component EII varies in type depending on organisms, however, with respect to enteric bacteria and coryneform bacteria, with which a research has been advanced, major EII enzymes are being identified, and among these, a fructose-specific EII is known to be encoded by FruA (PtsF) (Non-Patent Document 5).

It is known that the fructose uptake by the PTS system requires FruA which externally take up fructose and converts it into fructose 1-phosphate as well as FruK (PfkB) which converts fructose 1-phosphate into fructose 1,6-bis-phosphate serving as an important intermediate in glycolysis (Non-Patent Documents 6 and 7).

With respect to the production of a substance, several reports in which the productivity is improved by modifying the PTS system have been known. For example, a process for producing an amino acid using a bacterium of the genus *Escherichia* with enhanced ptsG gene (Patent Document 1), and a process for producing an amino acid using a bacterium of the genus *Escherichia* with enhanced crr gene which functions in the same manner as ptsH, ptsI, and, ptsG (Patent Document 2) are known.

Further, a method for accelerating uptake and metabolism of a sugar which does not go through the PTS system, such as pentose or the like, by disrupting the PTS system which is the uptake system of the major sugar, glucose or the like, is known (Patent Document 3).

Further, it is known that the productivity of a target substance can be increased by disrupting the PTS system, which is the glucose uptake system, to lead to uptake via another pathway and thereby changing the metabolic pathway of the sugar (Patent Document 4). It is also known that the productivity can be increased by disrupting the fructose uptake system and introducing a foreign fructokinase and thereby changing the metabolic pathway of the sugar (Non-Patent Document 5).

However, it has not been known that a target substance can be efficiently produced by disrupting the PTS uptake system of a specific sugar to improve the ability of uptake of another sugar by the PTS system. Further, it has not been known that the ability of uptake of another sugar is increased when the PTS uptake system and a metabolic pathway after uptake are disrupted simultaneously. In particular, since glucose plays a central role in controlling sugar uptake, even if the uptake system is simply enhanced, there arises a problem that the uptake rate decreases as the intracellular glucose concentration increases, and therefore, it has been predicted that it is difficult to improve a glucose consumption rate (Non-Patent Document 8).

CITATION LIST

Patent Documents

Patent Document 1: WO 03/04670
Patent Document 2: WO 03/04674
Patent Document 3: JP-A-5-49441
Patent Document 4: U.S. patent application Publication No. 2009/0142843

Non Patent Documents

Non-Patent Document 1: Mol. Microbiol., 35, 699 (2000)
Non-Patent Document 2: Microbiol. Rev., 57, 543 (1993)
Non-Patent Document 3: J. Bacteriol., 174, 1433 (1992)
Non-Patent Document 4: Biochem. Soc. Trans., 33, 220 (2005)
Non-Patent Document 5: FEMS Microbiol. Lett., 244, 259 (2005)
Non-Patent Document 6: Advan, Enzyme Regul. 42, 349, (2002)
Non-Patent Document 7: Eur. J. Biochem., 254, 96 (1998)
Non-Patent Document 8: FEMS Microbiol. Rev., 32, 891 (2008)

SUMMARY OF THE INVENTION

Problems to be Solved by the Invention

An object of the invention is to improve a sugar consumption rate when producing a useful substance by a fermentation process using a coryneform bacterium.

Means for Solving the Problems

The present invention relates the following (1) to (6).

(1) A process for producing a target substance comprising: culturing, in a medium, a coryneform bacterium in which the activity of a PTS protein relating to fructose uptake is reduced or lost as compared with a parent strain and the bacterium can produce the target substance, allowing the target substance to form and accumulate in a culture; and collecting the target substance from the culture.

(2) The process described in above (1), wherein the coryneform bacterium in which the activity of a PTS protein relating to fructose uptake is reduced or lost as compared with a parent strain and the bacterium can produce the target substance is a coryneform bacterium in which the activity of the protein is reduced or lost as compared with a parent strain by introducing a deletion, a substitution, or an addition of a base into a gene encoding the protein in the chromosomal DNA of the parent strain.

(3) The process described in above (1) or (2), wherein the PTS protein relating to fructose uptake is a protein containing FruK protein and FruA protein.

(4) The process described in any one of above (1) to (3), wherein the coryneform bacterium is *Corynebacterium glutamicum*.

(5) The process described in any one of above (1) to (4), wherein the target substance is an amino acid, a peptide, or a protein.

(6) The process described in any one of above (1) to (5), wherein the amino acid is an amino acid selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine.

Effects of the Invention

According to the present invention, a target substance can be efficiently produced by using a fermentation process.

EMBODIMENTS FOR CARRYING OUT THE INVENTION

1. Coryneform Bacterium to be Used in the Invention

The coryneform bacterium to be used in the invention is a coryneform bacterium in which the activity of a PTS protein relating to fructose uptake is reduced or lost as compared with a parent strain and the bacterium can produce a target substance.

The coryneform bacterium in which the activity of a PTS protein relating to fructose uptake is reduced or lost as compared with a parent strain is obtained by introducing a deletion, a substitution, or an addition of a base into a base sequence of a gene encoding the wild-type PTS protein relating to fructose uptake, which is present in the chromosomal DNA and has no mutation, and examples thereof can include: (a) a coryneform bacterium in which the activity of the PTS protein relating to fructose uptake is reduced to 80% or less, preferably 50% or less, more preferably 30% or less, further more preferably 20% or less, particularly preferably 10% or less, and most preferably 0% as compared with the parent strain; and (b) a coryneform bacterium in which the transcription amount of the gene or the production amount of the PTS protein relating to fructose uptake is reduced to 80% or less, preferably 50% or less, more preferably 30% or less, further more preferably 20% or less, particularly preferably 10% or less, and most preferably 0% as compared with the parent strain. More preferred examples thereof can include a coryneform bacterium in which the gene encoding FruK protein or FruA protein is partially or completely deleted.

The gene encoding FruA protein may be any gene as long as it encodes a polypeptide having FruA activity involved in fructose uptake and a reaction of conversion of fructose into fructose 1-phosphate. The gene encoding FruK protein may be any gene as long as it is a DNA encoding a polypeptide having FruK activity involved in a reaction of conversion of fructose 1-phosphate into fructose 1,6-bisphosphate. Specific examples thereof can include the following genes:

[1] a gene encoding a protein comprising the amino acid sequence represented by SEQ ID NO:1;

[2] a gene encoding a protein comprising the amino acid sequence represented by SEQ ID NO:2;

[3] a gene encoding a protein having 80% or more, preferably 90% or more, more preferably 95% or more, further more preferably 97% or more, particularly preferably 98% or more, and most preferably 99% or more identity to the amino acid sequence represented by SEQ ID NO:1, and shows fructose uptake activity along with a protein comprising the amino acid sequence represented by SEQ ID NO:2;

[4] a gene encoding a protein having 80% or more, preferably 90% or more, more preferably 95% or more, further more preferably 97% or more, particularly preferably 98% or more, and most preferably 99% or more identity to the amino acid sequence represented by SEQ ID NO:2, and shows fructose uptake activity along with a protein comprising the amino acid sequence represented by SEQ ID NO:1;

[5] a gene comprising the base sequence represented by SEQ ID NO:3;

[6] a gene comprising the base sequence represented by SEQ ID NO:4;

[7] a gene which hybridizes with a DNA consisting of a base sequence complementary to the base sequence represented by SEQ ID NO:3 under stringent conditions, and encodes a protein showing fructose uptake activity along with a protein comprising the amino acid sequence represented by SEQ ID NO:2; and

[8] a gene which hybridizes with a DNA consisting of a base sequence complementary to the base sequence represented by SEQ ID NO:4 under stringent conditions, and encodes a protein showing fructose uptake activity along with a protein comprising the amino acid sequence represented by SEQ ID NO:1.

The gene as used herein refers to a DNA which may contain a transcriptional regulatory region, a promoter region, and the like in addition to a coding region of a protein.

The transcriptional regulatory region may include a DNA consisting of 100 bases, preferably 50 bases upstream of the 5' end of a coding region in a chromosomal DNA. The promoter region may include a region corresponding to −10 and −35 region.

In the introduction of a deletion, a substitution, or an addition of a base into a gene encoding a PTS protein relating to fructose uptake, the type of the base and the number of the bases are not limited as long as the deletion, substitution, or addition of a base causes reduction or loss of the activity as compared with a parent strain. The deletion of a base may include, in the case of a promoter or a transcriptional regulatory region, a deletion of preferably 10 bases or more, more preferably 20 bases or more, and further more preferably the whole of the region, and in the case of a coding region, a deletion of preferably 10 bases or more, more preferably 20 bases or more, further more preferably 100 bases or more, particularly preferably 200 bases or more, and most preferably the whole of the coding region.

The substitution of a base may include, a substitution of a base within the 150 bases, preferably a base within the 100 bases, more preferably a base within the 50 bases, particularly preferably a base within the 30 bases, and most preferably a base within the 20 bases from the 5' end of a coding region to introduce a nonsense codon [An Introduction to Genetic Analysis 7th edition, W. H. Freeman (2000)].

The addition of a base may include, an addition of a DNA fragment of 50 bases or more, preferably 100 bases or more, more preferably 200 bases or more, further more preferably 500 bases or more, and particularly preferably 1 kb or more to a site immediately downstream of a base within the 150 bases, preferably a base within the 100 bases, more preferably a base within the 50 bases, particularly preferably a base within the 30 bases, and most preferably a base within the 20 bases from the 5' end of a coding region. Particularly preferable examples may include an insertion of a chloramphenicol resistance gene, a kanamycin resistance gene, or the like.

The identity of amino acid sequences or base sequences can be determined using the algorithm BLAST by Karlin and Altschul [Proc. Natl. Acad. Sci. USA, 90, 5873 (1993)] or FASTA [Methods Enzymol., 183, 63 (1990)]. Based on the algorithm BLAST, programs called BLASTN and BLASTX have been developed [J. Mol. Biol., 215, 403 (1990)]. In the case where a base sequence is analyzed using BLASTN based on BLAST, the parameters are set, for example, as follows: score=100 and word length=12. In the case where an amino acid sequence is analyzed using BLASTX based on BLAST, the parameters are set, for example, as follows: score=50 and word length=3. In the case where BLAST and Gapped BLAST programs are used, default parameters for each of the programs are employed. The specific methods for these analytical methods are well known.

Whether or not the bacterium is a coryneform bacterium in which the activity of a PTS protein relating to fructose uptake is reduced or lost as compared with a parent strain can be confirmed by, for example, comparing the transcription amount of a gene encoding the PTS protein relating to fructose uptake by using Northern blotting or the production amount of the PTS protein relating to fructose uptake by using Western blotting between the bacterium and the parent strain.

Further, whether or not the bacterium is a coryneform bacterium in which the activity of a PTS protein relating to fructose uptake is reduced or lost as compared with a parent strain can be confirmed by observing that when the bacterium is cultured in a medium containing fructose as a single carbon source, the bacterium does not grow or grows poorly as compared with the parent strain.

The "hybridization" as used above refers to hybridization of a DNA with a DNA having a specific base sequence or a part of the DNA. Therefore, the DNA comprising a specific base sequence or a part thereof is a DNA which can be used as a probe in a Northern or Southern blot analysis, and also can be used as an oligonucleotide primer in a PCR analysis. The DNA to be used as a probe may include a DNA of at least 100 bases or more, preferably 200 bases or more, and more preferably 500 bases or more. The DNA to be used as a primer may include a DNA of at least 10 bases or more, and preferably 15 bases or more.

A method for DNA hybridization experiment is well known, and for example, according to the specification of this application, the conditions for hybridization can be determined by those skilled in the art. The conditions for hybridization is described in Molecular Cloning, 2nd and 3rd Ed. (2001), Methods for General and Molecular Bacteriology, ASM Press (1994), or Immunology methods manual, Academic press (1996), and also, hybridization can be performed according to any of a number of other standard textbooks.

Further, also according to an instructional manual accompanying a commercially available hybridization kit, a DNA which hybridizes under stringent conditions can be obtained. The commercially available hybridization kit may include, for example, a kit with which a probe is produced by a random prime method, and hybridization is performed under stringent conditions.

The above-described stringent conditions are preferably conditions in which a filter on which a DNA has been immobilized and a probe DNA are incubated overnight at 42° C. in a solution containing 50% formamide, 5×SSC (750 mmol/l sodium chloride and 75 mmol/l sodium citrate), 50 mmol/l sodium phosphate (pH 7.6), 5×Denhardt's solution, 10% dextran sulfate, and 20 µg/l of a denatured salmon sperm DNA, and then the filter is washed in, for example, a 0.2×SSC solution at about 65° C., however, less stringent conditions can also be used. The stringent conditions can be changed by adjusting the formamide concentration (as the formamide concentration is decreased, the stringency is decreased) or by changing the salt concentration and the temperature conditions. The low stringent conditions may include, for example, conditions in which incubation is performed overnight at 37° C. in a solution containing 6×SSCE (20×SSCE contains 3 mol/l sodium chloride, 0.2 mol/l sodium dihydrogen phosphate, and 0.02 mol/l EDTA at pH 7.4), 0.5% SDS, 30% formamide, and 100 µg/l of a denatured salmon sperm DNA, and then washing is performed using a solution containing 1×SSC and 0.1% SDS at 50° C. Further, the lower stringent conditions may include conditions in which in the above-described low stringent conditions, hybridization is performed using a solution having a high salt concentration (for example, 5×SSC), and then washing is performed.

The above-described various conditions can also be set by adding or changing a blocking reagent to be used for suppressing the background in the hybridization experiment. The addition of the blocking reagent may be accompanied by a change in hybridization conditions for adapting the conditions.

The DNA which can hybridize under the above-described stringent conditions may include a DNA having at least 90% or more, preferably 95% or more, more preferably 97% or more, further more preferably 98% or more, and particularly preferably 99% or more identity to a DNA consisting of a base sequence represented by SEQ ID NO:3 or 4 when performing calculation based on the above-described parameters and the like using, for example, BLAST, FASTA, or the like.

The phrase "can produce a target substance" refers to an ability to produce a target substance when a coryneform bacterium to be used in the invention is cultured in a medium to such an extent that the target substance can be collected from the cells or the medium.

The coryneform bacterium which can produce a target substance may include, in the case where a parent strain originally has a property capable of producing a target substance, a coryneform bacterium in which the property has been enhanced, and in the case where a parent strain does not have the property, a coryneform bacterium to which the property has been artificially imparted.

The coryneform bacterium to be used in the invention may include a coryneform bacterium belonging to the genus *Corynebacterium*, the genus *Brevibacterium*, or the genus *Microbacterium*.

Examples of a microorganism belonging to the genus *Corynebacterium* may include *Corynebacterium glutamicum, Corynebacterium acetoacidophilum, Corynebacterium acetoglutamicum, Corynebacterium callunae, Corynebacterium herculis, Corynebacterium lilium, Corynebacterium melassecola, Corynebacterium thermoaminogenes* and the like, and specific examples thereof may include *Corynebac-* terium glutamicum ATCC 13032, Corynebacterium glutamicum ATCC 13060, Corynebacterium glutamicum ATCC 13826 (former name: Brevibacterium flavum), Corynebacterium glutamicum ATCC 14020 (former name: Brevibacterium divaricatum), Corynebacterium glutamicum ATCC 13869 (former name: Brevibacterium lactofermentum), Corynebacterium acetoacidophilum ATCC 13870, Corynebacterium acetoglutamicum ATCC 15806, Corynebacterium callunae ATCC 15991, Corynebacterium herculis ATCC 13868, Corynebacterium lilium ATCC 15990, Corynebacterium melassecola ATCC 17965, Corynebacterium thermoaminogenes ATCC 9244 and the like.

Examples of a microorganism belonging to the genus Brevibacterium may include Brevibacterium saccharolyticum, Brevibacterium immariophilum, Brevibacterium roseum, Brevibacterium thiogenitalis and the like, and specific examples thereof may include Brevibacterium saccharolyticum ATCC 14066, Brevibacterium immariophilum ATCC 14068, Brevibacterium roseum ATCC 13825, Brevibacterium thiogenitalis ATCC 19240 and the like.

Examples of a microorganism belonging to the genus Microbacterium may include Microbacterium ammoniaphilum and the like, and specific examples thereof may include Microbacterium ammoniaphilum ATCC 15354 and the like.

2. Process for Producing Coryneform Bacterium of the Invention

The coryneform bacterium of the invention can be obtained by using a coryneform bacterium which can produce a target substance and has the activity of FruK protein and FruA protein (hereinafter also referred to as FruKA activity) as a parent strain, and reducing or deleting the FruKA activity of the parent strain by using a method capable of introducing a mutation into a coryneform bacterium such as a usual mutation treatment method, a gene substitution method by a recombinant DNA technique or the like, a cell fusion method, or a transduction method; a method capable of suppressing the expression of a gene encoding FruK protein and FruA protein such as an antisense method; or the like.

The parent strain may be a wild-type strain or a breeding strain which has been artificially bred from the wild-type strain as long as it is a coryneform bacterium which has an ability to produce a target substance and also has FruKA activity.

Examples of the method for artificially imparting an ability to produce a target substance to a coryneform bacterium may include:

(a) a method of relieving or canceling at least one mechanism of controlling the biosynthesis of the target substance;

(b) a method of enhancing the expression of at least one enzyme involved in the biosynthesis of the target substance;

(c) a method of increasing the number of copies of at least one gene encoding an enzyme involved in the biosynthesis of the target substance;

(d) a method of attenuating or blocking at least one metabolic pathway branching from the biosynthetic pathway of the target substance into a metabolite other than the target substance; and (e) a method of selecting a cell line having higher degree of resistance to an analog of the target substance as compared with the wild-type strain.

The above described known methods can be used alone or in combination with one another.

As a method for preparing a coryneform bacterium which has an ability to produce a target substance, in particular, in the case where the target substance is an amino acid, a method for preparing a coryneform bacterium which has an ability to produce the amino acid, using any of the above-described methods (a) to (e) or a method in combination thereof, a lot of examples are described in Biotechnology 2nd ed., Vol. 6, Products of Primary Metabolism (VCH Verlagsgesellschaft mbH, Weinheim, 1996) section 14a, 14b or Advances in Biochemical Engineering/Biotechnology, 79, 1-35 (2003), Agric. Biol, Chem., 51, 2089-2094 (1987), and Amino Acid Fermentation, Gakkai Shuppan Center, Hiroshi Aida, et al., (1986). Further, other than the above-described publications, a specific method for preparing a coryneform bacterium which has an ability to produce an amino acid has been reported in a lot of publications such as JP-A-2003-164297, Agric. Biol. Chem., 39, 153-160 (1975), Agric. Biol. Chem., 39, 1149-1153 (1975), JP-A-58-13599, J. Gen. Appl. Microbiol., 4, 272-283 (1958), JP-A-63-94985, Agric. Biol. Chem., 37, 2013-2023 (1973), WO 97/15673, JP-A-56-18596, JP-A-56-144092, JPA-2003-511086, and WO 2006/001380, and the coryneform bacterium which has an ability to produce an amino acid can be prepared with reference to any of the above-described publications, etc.

Examples of the coryneform bacterium which has an ability to produce L-arginine prepared by the above-described method may include Corynebacterium glutamicum RB2631 (WO 2006/035831), and examples of the coryneform bacterium which has an ability to produce L-lysine prepared by the above-described method may include Corynebacterium glutamicum AHP-3 (FERM BP-7382).

A coryneform bacterium which can be used for preparing the above-described coryneform bacterium having an ability to produce a target substance may be any bacterium as long as it is a coryneform bacterium to which any of the above-described methods (a) to (e) can be applied or a coryneform bacterium which has the above-described genetic characteristics, and preferable examples thereof may include the above-described coryneform bacterium belonging to the genus Corynebacterium, the genus Brevibacterium, or the genus Microbacterium.

Examples of the mutation treatment method may include a method using N-methyl-N'-nitro-N-nitrosoguanidine (NTG) (Microorganism Experiment Manual, 1986, p. 131, Kodansha Scientific, Ltd.) and a UV irradiation method and the like.

Examples of the gene substitution method by a recombinant DNA technique may include a method in which a substitution, a deletion, or an addition of one or more bases is introduced into a gene encoding FruK protein and FruA protein (hereinafter also referred to as FruKA gene) in vitro, the gene is integrated into the chromosome of a parent strain by homologous recombination or the like, and further, the FruKA gene originally present in the chromosome is substituted by homologous recombination or the like.

Examples of the method for introducing a substitution, a deletion, or an addition of one or more bases into the FruKA gene may include a method in accordance with a site-specific mutagenesis method described in, for example, Molecular cloning: a laboratory manual, 3rd ed., Cold Spring Harbor Laboratory Press (2001) (hereinafter abbreviated as Molecular cloning 3rd ed.), Current Protocols in Molecular Biology, John Wiley & Sons (1987-1997) (hereinafter abbreviated as Current Protocols in Molecular Biology), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), or the like.

The gene substitution by a recombinant DNA technique can be performed by introducing a mutation into the FruKA gene according to the method described in J. Bacteriol., 182, 6884 (2000) or the like.

The FruKA gene can be obtained by the PCR method or the like based on the known information of the base sequence of the FruKA gene derived from *Corynebacterium glutamicum* [for example, the National Center for Biotechnology Information (NCBI) accession numbers: NC_006958 REGION: 2012568 to 2013560, NC_006958 REGION: 2013557 to 2015623].

By inserting the FruKA gene into which the mutation has been introduced (hereinafter referred to as mutant gene) into an appropriate plasmid vector or the like, a recombinant plasmid is produced.

As the plasmid vector, for example, a plasmid which cannot autonomously replicate in the parent strain, and has an antibiotic resistance marker gene and a levan sucrase gene sacB of *Bacillus subtilis* [Mol. Microbiol., 6, 1195 (1992)] can be used.

As the method for introducing the recombinant plasmid having the mutant DNA into the parent strain, any method can be used as long as it is a method capable of introducing a DNA into a coryneform bacterium, and examples thereof may include an electroporation method [Appl. Microbiol. Biotech., 52, 541 (1999)] a protoplast method [J. Bacteriol., 159, 306 (1984)] and the like.

Since the recombinant plasmid cannot autonomously replicate in the parent strain, by obtaining a strain which shows resistance to an antibiotic corresponding to the antibiotic resistance marker contained in the recombinant plasmid, a transformant strain in which the recombinant plasmid has been integrated into the chromosome can be obtained.

Further, by a selection method utilizing the fact that the levan sucrase of *Bacillus subtilis* integrated in the chromosome along with the mutant gene produces a suicide substrate [J. Bacteriol., 174, 5462 (1992)], a strain in which the FruKA gene in the chromosome of the parent strain has been substituted with the mutant gene can be obtained.

By the above-described method, the substitution of a gene in the chromosome of a parent strain can be performed, however, it is not limited to the above-described method, and another gene substitution method can also be used as long as it is a method capable of substituting a gene in the chromosome of a coryneform bacterium.

Examples of the method for introducing a substitution, a deletion, or an addition into the FruKA gene in the chromosome of the parent strain may include a fusion method and a transduction method other than the above-described methods, and for example, the method described in Amino Acid Fermentation, Gakkai Shuppan Center, edited by Hiroshi Aida, et al., (1986).

The number of bases for introducing a mutation is not limited as long as it is the number capable of reducing or deleting the FruKA activity by introducing a substitution, a deletion, or an addition of bases into the FruKA gene. The site where the mutation is introduced is not necessarily limited to a site in the base sequence of a coding region of the FruKA gene as long as it is a site capable of reducing or deleting the FruKA activity by the mutation, and may be in a transcriptional/translational regulatory region of the FruKA gene, but is preferably a coding region of the FruKA gene.

Examples of the method for reducing or losing the FruKA activity by introducing a substitution of a base may include a method for introducing a nonsense mutation.

The method for introducing a nonsense mutation may include, for example, a method in which PCR is performed using a primer containing a stop codon and the FruKA gene, and the FruKA gene in the chromosome of a parent strain is substituted using the obtained FruKA gene into which a nonsense mutation has been introduced.

Examples of the method for reducing or deleting the FruKA activity by introducing a deletion of a base sequence may include a method in which a mutant FruKA gene obtained by cleaving the FruK gene and the FruA gene with a restriction enzyme or the like, deleting a base sequence composed of an appropriate number of bases, and then, ligating the resulting fragments again is integrated into the chromosome.

A strain in which the FruKA activity has been reduced or lost can be obtained by utilizing the fact that the strain in which the FruKA activity has been reduced or lost grows slowly or cannot grow in a medium containing fructose as a single carbon source, and therefore obtaining a strain which grows in the same manner as the parent strain in the case where glucose is used as a single carbon source but does not grow or grows extremely poorly as compared with the parent strain in a medium in which fructose is used as a single carbon source among the coryneform bacteria into which the mutation has been introduced.

The method for selecting a coryneform bacterium in which the FruKA activity is reduced or lost can also be used as a method for selecting a coryneform bacterium which has an improved sugar consumption rate as compared with the parent strain and therefore is more suitable for producing a useful substance.

By culturing the thus obtained coryneform bacterium in which the bacterium has an ability to produce a target substance and the FruKA activity has been reduced or lost as compared with the parent strain, allowing the target substance to produce and accumulate in a culture, and collecting the target substance, the target substance can be produced. The coryneform bacterium to be used in the invention is also a coryneform bacterium whose sugar consumption rate has been improved, and therefore, the target substance can be efficiently produced.

The culturing of the coryneform bacterium can be performed by a conventional method for culturing a bacterium having an ability to produce a target substance.

As the medium, either of a synthetic medium or a natural medium can be used as long as it is a medium containing appropriate amounts of a carbon source, a nitrogen source, inorganic salts, and the like.

As the carbon source, mainly glucose can be used. A sugar which is taken up via the PTS system other than glucose can also be used, however, since the FruKA activity has been reduced or lost, it is not preferred to use sucrose or fructose.

As the nitrogen source, ammonia, any of a variety of inorganic and organic ammonium salts such as ammonium chloride, ammonium sulfate, ammonium carbonate, and ammonium acetate, urea, another nitrogen-containing compound, or a nitrogen-containing organic substance such as meat extract, yeast extract, corn steep liquor, or soybean hydrolysate can be used.

As the inorganic salt, monopotassium phosphate, potassium secondary phosphate, ammonium sulfate, sodium chloride, magnesium sulfate, calcium carbonate, or the like can be used.

Other than these, a minor nutrient source such as biotin, thiamin, nicotinamide, or nicotinic acid may be added as needed. Such a minor nutrient source can also be substituted with a medium additive such as meat extract, yeast extract, corn steep liquor, casamino acid or the like.

The culturing is performed under aerobic conditions such as shaking culture or submerged spinner culture under aeration. In general, the culturing temperature is preferably from 20 to 42° C., and more preferably from 30 to 40° C. The pH of the medium is preferably maintained around a neutral pH in a range from 5 to 9. The pH of the medium is adjusted with an inorganic or organic acid, an alkaline solution, urea, calcium carbonate, ammonia, a pH buffer, or the like.

The culturing period is generally from 1 to 6 days.

The collection of the target substance from the culture after completion of the culturing does not require a special method. That is, the extracellularly accumulated target substance can be collected by combining conventionally known ion exchange resin method, precipitation method, and other methods according to the type of the target substance. Further, the intracellularly accumulated target substance can be collected by physically or enzymatically disrupting the bacterial cells, and collecting the target substance from the bacterial cell homogenate or membrane fraction according to the type of the target substance. Incidentally, depending on the target substance, it is also possible to use the target substance in a state of being present in the bacterial cells as a microbial catalyst or the like.

The useful substance which can be produced according to the invention is not particularly limited, but examples thereof may include amino acids, peptides, and proteins.

Examples of the amino acid may include L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine, and preferred examples thereof can include L-aspartic acid, L-glutamic acid, and L-amino acids obtained by biosynthesis through L-aspartic acid, L-glutamic acid, or pyruvic acid in a microbial metabolic pathway.

Examples of the L-amino acid obtained by biosynthesis through L-aspartic acid may include L-methionine, L-lysine, L-threonine, L-asparagine and the like, and examples of the L-amino acid obtained by biosynthesis through L-glutamic acid may include L-glutamine, L-arginine, L-ornithine, L-proline and the like. Examples of the L-amino acid obtained by biosynthesis through pyruvic acid may include L-alanine, L-valine, L-leucine, L-isoleucine and the like.

Examples of the peptide may include dipeptides such as alanyl glutamine and carnosine and tripeptides such as glutathione, and examples of the protein may include biologically active polypeptides such as G-CSF, erythropoietin, and HGF.

Hereinafter, Examples of the invention will be described, however, the invention is not limited to these Examples.

Example 1

(1) Construction of Plasmid for Gene Disruption

A plasmid pHSG299 [Gene, 61, 63 (1987)] having a gene imparting kanamycin resistance was treated with PstI. Then, a DNA fragment of 2.6 kilobase pairs (hereinafter abbreviated as kb) containing a levan sucrase gene sacB derived from *Bacillus subtilis* [Mol. Microbiol., 6, 1195 (1992)] was ligated to the plasmid at the cleavage site, whereby a plasmid pESB30 was obtained.

(2) Construction of Plasmid for Creating fruKA Gene Disruption Strain

According to the method of Saito et al. [Biochim. Biophys. Acta, 72, 619 (1963)], a chromosomal DNA of a *Corynebacterium glutamicum* ATCC 13032 strain was prepared. By using the chromosomal DNA as a template, and also using each of a combination of a DNA consisting of a base sequence represented by SEQ ID NO:5 with a DNA consisting of a base sequence represented by SEQ ID NO:6, and a combination of a DNA consisting of a base sequence represented by SEQ ID NO:7 with a DNA consisting of a base sequence represented by SEQ ID NO:8 as a primer set, 2 types of PCR reactions were performed using PrimeSTAR Max DNA Polymerase (manufactured by Takara Bio, Inc.) and an accompanying buffer. Two PCR products of about 0.5 kb obtained by the PCR were electrophoresed on an agarose gel, respectively, and extracted using Wizard® SV Gel and PCR Clean-Up System (manufactured by Promega Co., Ltd.), and purified.

Further, by using each of the two purified products as a template, PCR was performed using a DNA consisting of a base sequence represented by SEQ ID NO:5 and a DNA composed of a base sequence represented by SEQ ID NO:8 as a primer set. The obtained PCR product was electrophoresed on an agarose gel, and extracted using Wizard® SV Gel and PCR Clean-Up System, and purified, whereby a DNA fragment of about 1.0 kb was obtained. The obtained DNA fragment was treated with a restriction enzyme using a restriction enzyme Sse8387I (manufactured by Takara Bio, Inc.) and an accompanying buffer. The obtained fragment treated with the restriction enzyme was extracted using Wizard® SV Gel and PCR Clean-Up System, and purified.

At the same time, the previously created pESB30 was treated with Sse8387I, and mixed with the obtained fragment treated with the restriction enzyme, and then, a ligase reaction was performed using a ligation kit Ver.1 (manufactured by Takara Bio, Inc.). By using the reaction product, an *Escherichia coli* DH5α strain (manufactured by Toyobo Co., Ltd.) was transformed according to a common procedure. The strain was cultured on an LB agar medium [a medium containing 10 g of Bacto trypton (manufactured by Difco Co., Ltd.), 5 g of yeast extract (manufactured by Difco Co., Ltd.), 10 g of sodium chloride, and 16 g of Bacto agar (manufactured by Difco Co., Ltd.) in 1 L of water, and adjusted to pH 7.0] containing 20 μg/ml kanamycin, and a transformant strain was selected. The transformant strain was cultured overnight with an LB medium containing 20 μg/ml kanamycin, and the plasmid was prepared by the alkali SDS method (Molecular cloning 3rd ed.) from the obtained culture broth. The thus obtained plasmid was named pDfruKA.

(3) Creation of FruKA Gene Disruption Strain

By using the plasmid pDfruKA prepared in (2), a *Corynebacterium glutamicum* ATCC 13032 strain was transformed by the electroporation method according to the method of Rest et al. [Appl. Microbiol. Biotech., 52, 541 (1999)], and kanamycin resistant strains were selected. It is presumed that in the kanamycin resistant strains, pDfruKA has been integrated into the chromosome of each of the strains by Campbell-type homologous recombination. In such a strain, a DNA encoding fruKA originally present in the chromosome and a DNA having a structure in which fruKA in pDfruKA has been disrupted are present in proximity to each other, and the second homologous recombination is easy to occur therebetween.

Since levan sucrose encoded by sacB converts sucrose into a suicide substrate, a microorganism having sacB cannot grow in a medium containing sucrose. However, a strain in which the second homologous recombination has occurred between a DNA in a region around the fruKA gene originally present in the chromosome and a DNA having a structure in which the fruKA gene in pDfruKA has been disrupted, either DNA is deleted along with sacB, and therefore, the strain can grow even in a medium containing sucrose. In this manner, a microorganism in which the fruKA gene originally present in the chromosome of a host microorganism is deleted can be obtained.

By utilizing this, the above-described transformant strain was applied on a Suc agar medium [a medium containing 100 g of sucrose, 7 g of meat extract, 10 g of peptone, 3 g of sodium chloride, 5 g of yeast extract (manufactured by Difco Co., Ltd.), and 15 g of Bacto agar (manufactured by Difco Co., Ltd.) in 1 L of water, and adjusted to pH 7.2], and cultured at 30° C. for 1 day, and then, colonies which grew were selected.

Each of the thus obtained colonies was inoculated in a medium containing fructose as a single carbon source [a medium containing 4 g of ammonium chloride, 1 g of monopotassium phosphate, 3 g of dipotassium phosphate, 2 g of urea, 100 mg of biotin, 5 mg of thiamine hydrochloride, 5 mg of nicotinic acid, 10 mg of iron sulfate heptahydrate, 1 mg of zinc sulfate heptahydrate, 0.2 mg of copper sulfate pentahydrate, 1 mg of manganese sulfate pentahydrate, 10 mg of calcium chloride, 10 g of fructose, 0.4 g of magnesium sulfate, and 15 g of Bacto agar (manufactured by Difco Co., Ltd.) in 1 L of water, and adjusted to pH 7.2], and a colony which grew poorly or could not grow was obtained and named WTΔfruKA strain.

(4) Creation of FruA Gene Disruption Strain

By using the same method as in the case of disrupting the FruKA gene, a strain in which only the FruA gene of a *Corynebacterium glutamicum* ATCC 13032 strain (hereinafter referred to as WT strain) was disrupted was also created as a control.

The creation of a plasmid for FruA gene disruption was performed in the same manner as in the case of the FruKA gene disruption strain except that DNAs consisting of base sequences represented by SEQ ID NO:9 and SEQ ID NO:10 were used as a primer set instead of the DNAs consisting of base sequences represented by SEQ ID NO:6 and SEQ ID NO:7.

The thus created strain was inoculated in a medium containing fructose as a single carbon source, and a colony which grew poorly or could not grow was named WTΔfruA strain.

(5) Evaluation of WTΔfruKA Strain and WTΔfruA Strain

Each of the obtained WT strain, WTΔfruKA strain, and WTΔfruA strain was inoculated in a 2-L Erlenmeyer flask containing 6 g of calcium carbonate in 300 ml a seed medium (a medium containing 60 g of glucose, 5 g of corn steep liquor, 80 g of ammonium sulfate, 12 g of potassium monohydrogen phosphate, 4 g of magnesium sulfate heptahydrate, 40 mg of iron sulfate heptahydrate, 20 mg of manganese sulfate pentahydrate, 2 mg of copper sulfate, 2 mg of nickel chloride hexahydrate, 2 mg of cobalt chloride hexahydrate, 200 mg of calcium chloride dihydrate, 40 mg of hexaammonium heptamolybdate tetrahydrate, 40 mg of β-alanine, 40 mg of nicotinic acid, 40 mg of thiamine hydrochloride, and 0.4 mg of biotin in 1 L of water, and adjusted to pH 7.2), and cultured at 28° C. for 24 hours. 100 ml of this seed culture broth was inoculated in a jar fermenter containing 1150 ml of a main culture medium (a medium containing 60 g of glucose, 5 g of corn steep liquor, 80 g of ammonium sulfate, 12 g of potassium monohydrogen phosphate, 4 g of magnesium sulfate heptahydrate, 40 mg of iron sulfate heptahydrate, 20 mg of manganese sulfate pentahydrate, 2 mg of copper sulfate, 2 mg of nickel chloride hexahydrate, 2 mg of cobalt chloride hexahydrate, 200 mg of calcium chloride dihydrate, 40 mg of hexaammonium heptamolybdate, 40 mg of β-alanine, 40 mg of nicotinic acid, 40 mg of thiamine hydrochloride, and 0.4 mg of biotin in 1 L of water), and each strain was cultured at 33° C. The culturing was performed while adjusting the pH with an aqueous ammonia solution to maintain the pH at 6.7. The culturing was completed at the time when the glucose in the medium was completely consumed, and the culturing time at that time was measured.

As a result, as shown in Table 1, the sugar consumption rate was high in the case of the WTΔfruKA strain in which the FruKA gene was disrupted.

TABLE 1

Time required for completely consuming glucose at 6% contained at the beginning and the amount of cells at that time

| Strain | Time required for consumption (hour) | OD |
|---|---|---|
| WT | 13.5 | 65.3 |
| WTΔfruKA | 11.5 | 64.2 |
| WTΔfruA | 13.5 | 64.4 |

Example 2

Production of L-Arginine

As shown in Table 1, an effect of improving sugar consumption was obtained by disrupting the FruKA gene of the wild-type strain, and therefore, in order to confirm the application thereof to the production of a useful substance, a FruKA gene deletion strain of an RB2631 strain which is an L-arginine-producing strain (WO 2006/035831) was created, and the ability to produce arginine of the strain was examined.

By the same method as described in Example 1, an RB2631ΔfruKA strain which is a FruKA gene deletion strain of the RB2631 strain and an RB2631ΔfruA strain which is a FruA gene deletion strain of the RB2631 strain were created.

Each of these strains was cultured in a jar fermenter under the same conditions as described in Example 1. However, the culturing temperature was set to 37° C.

As a result, as shown in Table 2, it was shown that the sugar consumption rate and the productivity of L-arginine were high in the case of the RB2631ΔfruKA strain in which the FruKA gene was disrupted.

TABLE 2

Time required for completely consuming glucose at 6% contained at the beginning and the titer at that time

| Strain | Time required for consumption (hour) | OD | L-arginine (g/L) |
|---|---|---|---|
| RB2631 | 11 | 84.6 | 1.57 |
| RB2631ΔfruKA | 9 | 74.4 | 2.05 |
| RB2631ΔfruA | 15 | 79.8 | 1.59 |

TABLE 3

Time required for completely consuming glucose at 6% contained at the beginning and the titer at that time

| Strain | Time required for consumption (hour) | OD | L-lysine (g/L) |
|---|---|---|---|
| AHP-3 | 11 | 25.7 | 9.9 |
| AHP-3ΔfruKA | 9.5 | 26.7 | 12.8 |
| AHP-3ΔfruA | 14.5 | 23.2 | 11.6 |

Example 3

Examination Using L-Lysine-Producing Strain

A FruKA gene deletion strain and a FruA gene deletion strain of an AHP-3 strain (FERM BP-7382) which is an L-lysine-producing strain, wherein L-lysine is an amino acid whose biosynthetic pathway is different from that of L-arginine, were created, and the productivity of L-lysine thereof was examined.

By the same method as described in Example 1, an AHP-3ΔfruKA strain which is a FruKA gene deletion strain of the AHP-3 strain and an AHP-3ΔfruA strain which is a FruA gene deletion strain of the AHP-3 strain were created.

Each of these strains was cultured in a jar fermenter under the same conditions as described in Example 1.

As a result, as shown in Table 3, it was shown that the sugar consumption rate and the productivity of L-lysine were high in the case of the AHP-3ΔfruKA strain in which the FruKA gene was disrupted.

INDUSTRIAL APPLICABILITY

According to the present invention, a target substance can be efficiently produced by using a fermentation process.

SEQUENCE LISTING

SEQ ID NO:5—Description of Artificial Sequence: Synthetic DNA

SEQ ID NO:6—Description of Artificial Sequence: Synthetic DNA

SEQ ID NO:7—Description of Artificial Sequence: Synthetic DNA

SEQ ID NO:8—Description of Artificial Sequence: Synthetic DNA

SEQ ID NO:9—Description of Artificial Sequence: Synthetic DNA

SEQ ID NO:10—Description of Artificial Sequence: Synthetic DNA

The invention claimed is:

1. A process for producing a target substance, comprising:
culturing in a medium that contains glucose as a sole carbon source a coryneform bacterium in which the activity of both FruK protein and FruA protein are lost as compared with a parent strain, wherein the bacterium can produce the target substance;
allowing the target substance to form and accumulate in a culture; and
collecting the target substance from the culture, wherein the target substance is an amino acid, a peptide or a protein.

2. The process according to claim 1, wherein the lost activity of FruK protein and FruA protein is obtained by introducing a deletion, a substitution, or an addition of a base into genes encoding those proteins in the chromosomal DNA of the parent strain.

3. The process according to claim 1, wherein the coryneform bacterium is *Corynebacterium glutamicum*.

4. The process according to claim 2, wherein the coryneform bacterium is *Corynebacterium glutamicum*.

5. The process according to claim 1, wherein the target substance is an amino acid selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine.

6. The process according to claim 2, wherein the target substance is an amino acid selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine.

7. The process according to claim 3, wherein the target substance is an amino acid selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine.

8. The process according to claim 4, wherein the target substance is an amino acid selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, L-citrulline, L-glutamine, L-proline, L-serine, L-ornithine, L-methionine, L-aspartic acid, L-asparagine, and glycine.

* * * * *

UNITED STATES PATENT AND TRADEMARK OFFICE
CERTIFICATE OF CORRECTION

PATENT NO.       : 9,567,616 B2
APPLICATION NO.  : 13/983917
DATED            : February 14, 2017
INVENTOR(S)      : Tetsuro Ujihara et al.

It is certified that error appears in the above-identified patent and that said Letters Patent is hereby corrected as shown below:

In the Specification

Column 1:
Line 24, "A research" should read --Research--;
Line 30, "which phosphorylate and thereby take" should read
--that phosphorylates and thereby takes--;
Line 37, "organisms," should read --organisms;--; and
Line 38, "a" should be deleted; and
Line 43, "take" should read --takes--.

Column 2:
Line 28, "Non Patent" should read --Non-Patent--; and
Line 37, "Advan," should read --Advan.--.

Column 4:
Line 43, "region." should read --regions.--.

Column 5:
Line 58, "is" should read --are--.

Column 6:
Line 12, "65° C., however," should read --65° C.. However,--; and
Line 13, "used." should read --employed.--.

Column 7:
Line 64, "above described" should read --above-described--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*

Column 9:
Line 42, "performed," should read --performed;--.

Column 10:
Line 52, "used," should read --used;--.

Column 12:
Line 63, "Kanamycin resistant" should read --Kanamycin-resistant--; and
Line 64, "Kanamycin resistant" should read --Kanamycin-resistant--.

In the Claims

Column 29:
Line 47, "source" should read --source,--.

```
SEQUENCE LISTING

<160> NUMBER OF SEQ ID NOS: 10

<210> SEQ ID NO 1
<211> LENGTH: 993
<212> TYPE: DNA
<213> ORGANISM: Corynebacterium glutamicum
<220> FEATURE:
<221> NAME/KEY: CDS
<222> LOCATION: (1)..(993)

<400> SEQUENCE: 1 atg atc atc aca ttc acc cca aac ccg agt att gat tcc acg ctg tcg      48
Met Ile Ile Thr Phe Thr Pro Asn Pro Ser Ile Asp Ser Thr Leu Ser
1               5                   10                  15 ctc ggc gaa gag ctc tcc cgt gga tcc gtc caa cga ctt gat tcc gtc      96
Leu Gly Glu Glu Leu Ser Arg Gly Ser Val Gln Arg Leu Asp Ser Val
            20                  25                  30 acc gct gtc gca ggt ggt aaa ggc atc aat gtc gcc cac gct gtc ttg     144
Thr Ala Val Ala Gly Gly Lys Gly Ile Asn Val Ala His Ala Val Leu
        35                  40                  45 ctt gcg ggc ttt gaa acc ttg gct gtg ttc cca gcc ggc aag ctc gac     192
Leu Ala Gly Phe Glu Thr Leu Ala Val Phe Pro Ala Gly Lys Leu Asp
    50                  55                  60 ccc ttc gtc cca ctg gtc cgc gac atc ggc ttg ccc gtg gaa act gtt     240
Pro Phe Val Pro Leu Val Arg Asp Ile Gly Leu Pro Val Glu Thr Val
65                  70                  75                  80 gtg atc aac aag aac gtc cgc acc aac acc gtc acc gaa ccg gac         288
Val Ile Asn Lys Asn Val Arg Thr Asn Thr Val Thr Glu Pro Asp
                85                  90                  95 ggc acc acc acc aag ctc aac ggc ccc ggc gcg ccg ctc agc gag cag     336
Gly Thr Thr Thr Lys Leu Asn Gly Pro Gly Ala Pro Leu Ser Glu Gln
```

```
                100                 105                 110
aag ctc cgt agc ttg gaa aag gtg ctt atc gac gcg ctc cgc ccc gaa    384
Lys Leu Arg Ser Leu Glu Lys Val Leu Ile Asp Ala Leu Arg Pro Glu
            115                 120                 125 gtc acc tgg gtt gtc ctg gcg ggc tcg ctg cca cca ggg gca cca gtt    432
Val Thr Trp Val Val Leu Ala Gly Ser Leu Pro Pro Gly Ala Pro Val
        130                 135                 140 gac tgg tac gcg cgt ctc acc gcg ttg atc cat tca gca cgc cct gac    480
Asp Trp Tyr Ala Arg Leu Thr Ala Leu Ile His Ser Ala Arg Pro Asp
145                 150                 155                 160 gtt cgc gtg gct gtc gat acc tca gac aag cca ctg atg gcg ttg ggc    528
Val Arg Val Ala Val Asp Thr Ser Asp Lys Pro Leu Met Ala Leu Gly
                165                 170                 175 gag agc ttg gat aca cct ggc gct gct ccg aac ctg att aag cca aat    576
Glu Ser Leu Asp Thr Pro Gly Ala Ala Pro Asn Leu Ile Lys Pro Asn
            180                 185                 190 ggt ctg gaa ctg ggc cag ctg gct aac act gat ggt gaa gag ctg gag    624
Gly Leu Glu Leu Gly Gln Leu Ala Asn Thr Asp Gly Glu Glu Leu Glu
        195                 200                 205 gcg cgt gct gcg caa ggc gat tac gac gcc atc atc gca gct gcg gac    672
Ala Arg Ala Ala Gln Gly Asp Tyr Asp Ala Ile Ile Ala Ala Ala Asp
    210                 215                 220 gta ctg gtt aac cgt ggc atc gaa cag gtg ctt gtc acc ttg ggt gcc    720
Val Leu Val Asn Arg Gly Ile Glu Gln Val Leu Val Thr Leu Gly Ala
225                 230                 235                 240 gca gga gcg gtg ttg gtc aac gca gaa ggt gcg tgg act gct act tct    768
Ala Gly Ala Val Leu Val Asn Ala Glu Gly Ala Trp Thr Ala Thr Ser
                245                 250                 255 cca aag att gat gtt gta tcc acc gtt gga gct gga gac tgt gct ctt    816
Pro Lys Ile Asp Val Val Ser Thr Val Gly Ala Gly Asp Cys Ala Leu
            260                 265                 270 gca ggt ttt gtt atg gca cgt tcc cag aag aaa aca ctg gag gaa tct    864
Ala Gly Phe Val Met Ala Arg Ser Gln Lys Lys Thr Leu Glu Glu Ser
        275                 280                 285 ctg ctg aat gcc gtg tct tac ggc tcg act gcg gcg tct ctt cct ggc    912
Leu Leu Asn Ala Val Ser Tyr Gly Ser Thr Ala Ala Ser Leu Pro Gly
    290                 295                 300 act acc att cct cgt cct gac caa ctc gcc aca gct ggt gca acg gtc    960
Thr Thr Ile Pro Arg Pro Asp Gln Leu Ala Thr Ala Gly Ala Thr Val
305                 310                 315                 320 acc caa gtc aaa gga ttg aaa gaa tca gca tga                        993
Thr Gln Val Lys Gly Leu Lys Glu Ser Ala
                325                 330

<210> SEQ ID NO 2
<211> LENGTH: 2067
<212> TYPE: DNA
<213> ORGANISM: Corynebacterium glutamicum
<220> FEATURE:
<221> NAME/KEY: CDS
<222> LOCATION: (1)..(2067)

<400> SEQUENCE: 2 atg aat agc gta aat aat tcc tcg ctt gtc cgg ctg gat gtc gat ttc     48
Met Asn Ser Val Asn Asn Ser Ser Leu Val Arg Leu Asp Val Asp Phe
1               5                   10                  15 ggc gac tcc acc acg gat gtc atc aac aac ctt gcc act gtt att ttc     96
Gly Asp Ser Thr Thr Asp Val Ile Asn Asn Leu Ala Thr Val Ile Phe
            20                  25                  30 gac gct ggc cga gct tcc tcc gcc gac gcc ctt gcc aaa gac gcg ctg    144
Asp Ala Gly Arg Ala Ser Ser Ala Asp Ala Leu Ala Lys Asp Ala Leu
```

```
              35                  40                  45
gat cgt gaa gca aag tcc ggc acc ggc gtt cct ggt caa gtt gct atc       192
Asp Arg Glu Ala Lys Ser Gly Thr Gly Val Pro Gly Gln Val Ala Ile
 50                  55                  60 ccc cac tgc cgt tcc gaa gcc gta tct gtc cct acc ttg ggc ttt gct       240
Pro His Cys Arg Ser Glu Ala Val Ser Val Pro Thr Leu Gly Phe Ala
 65                  70                  75                  80 cgc ctg agc aag ggt gtg gac ttc agc gga cct gat ggc gat gcc aac       288
Arg Leu Ser Lys Gly Val Asp Phe Ser Gly Pro Asp Gly Asp Ala Asn
                 85                  90                  95 ttg gtg ttc ctc att gca gca cct gct ggc ggc ggc aaa gag cac ctg       336
Leu Val Phe Leu Ile Ala Ala Pro Ala Gly Gly Gly Lys Glu His Leu
            100                 105                 110 aag atc ctg tcc aag ctt gct cgc tcc ttg gtg aag aag gat ttc atc       384
Lys Ile Leu Ser Lys Leu Ala Arg Ser Leu Val Lys Lys Asp Phe Ile
        115                 120                 125 aag gct ctg cag gaa gcc acc acc gag cag gaa atc gtc gac gtt gtc       432
Lys Ala Leu Gln Glu Ala Thr Thr Glu Gln Glu Ile Val Asp Val Val
    130                 135                 140 gat gcc gtg ctc aac cca gca cca aaa acc acc gag cca gct gca gct       480
Asp Ala Val Leu Asn Pro Ala Pro Lys Thr Thr Glu Pro Ala Ala Ala
145                 150                 155                 160 ccg gct gcg gcg gcg gtt gct gag agt ggg gcg gcg tcg aca agc gtt       528
Pro Ala Ala Ala Ala Val Ala Glu Ser Gly Ala Ala Ser Thr Ser Val
                165                 170                 175 act cgt atc gtg gca atc acc gca tgc cca acc ggt atc gca cac acc       576
Thr Arg Ile Val Ala Ile Thr Ala Cys Pro Thr Gly Ile Ala His Thr
            180                 185                 190 tac atg gct gcg gat tcc ctg acg caa aac gcg gaa ggc cgc gat gat       624
Tyr Met Ala Ala Asp Ser Leu Thr Gln Asn Ala Glu Gly Arg Asp Asp
        195                 200                 205 gtg gaa ctc gtt gtg gag act cag ggc tct tcc gct gtc acc cca gtc       672
Val Glu Leu Val Val Glu Thr Gln Gly Ser Ser Ala Val Thr Pro Val
    210                 215                 220 gat ccg aag atc atc gaa gct gcc gac gcc gtc atc ttc gcc acc gac       720
Asp Pro Lys Ile Ile Glu Ala Ala Asp Ala Val Ile Phe Ala Thr Asp
225                 230                 235                 240 gtg gga gtt aaa gac cgc gag cgt ttc gct ggc aag cca gtc att gaa       768
Val Gly Val Lys Asp Arg Glu Arg Phe Ala Gly Lys Pro Val Ile Glu
                245                 250                 255 tcc ggc gtc aag cgc gcg atc aat gag cca gcc aag atg atc gac gag       816
Ser Gly Val Lys Arg Ala Ile Asn Glu Pro Ala Lys Met Ile Asp Glu
            260                 265                 270 gcc atc gca gcc tcc aag aac cca aac gcc cgc aag gtt tcc ggt tcc       864
Ala Ile Ala Ala Ser Lys Asn Pro Asn Ala Arg Lys Val Ser Gly Ser
        275                 280                 285 ggt gtc gcg gca tct gct gaa acc acc ggc gag aag ctc ggc tgg ggc       912
Gly Val Ala Ala Ser Ala Glu Thr Thr Gly Glu Lys Leu Gly Trp Gly
    290                 295                 300 aag cgc atc cag cag gca gtc atg acc ggc gtg tcc tac atg gtt cca       960
Lys Arg Ile Gln Gln Ala Val Met Thr Gly Val Ser Tyr Met Val Pro
305                 310                 315                 320 ttc gta gct gcc ggc ggc ctg ctg ttg gct ctc ggc ttc gca ttc ggt      1008
Phe Val Ala Ala Gly Gly Leu Leu Leu Ala Leu Gly Phe Ala Phe Gly
                325                 330                 335 gga tac gac atg gcg aac ggc tgg caa gca atc gcc acc cag ttc tct      1056
Gly Tyr Asp Met Ala Asn Gly Trp Gln Ala Ile Ala Thr Gln Phe Ser
            340                 345                 350 ctg acc aac ctg cca ggc aac acc gtc gat gtt gac ggc gtg gcc atg      1104
```

-continued

```
                Leu Thr Asn Leu Pro Gly Asn Thr Val Asp Val Asp Gly Val Ala Met
                            355                 360                 365 acc ttc gag cgt tca ggc ttc ctg ttg tac ttc ggc gca gtc ctg ttc        1152
Thr Phe Glu Arg Ser Gly Phe Leu Leu Tyr Phe Gly Ala Val Leu Phe
        370                 375                 380 gcc acc ggc caa gca gcc atg ggc ttc atc gtg gca gcc ctg tct ggc        1200
Ala Thr Gly Gln Ala Ala Met Gly Phe Ile Val Ala Ala Leu Ser Gly
385                 390                 395                 400 tac acc gca tac gca ctt gct gga cgc cca ggc atc gcg ccg ggc ttc        1248
Tyr Thr Ala Tyr Ala Leu Ala Gly Arg Pro Gly Ile Ala Pro Gly Phe
                405                 410                 415 gtc ggt ggc gcc atc tcc gtc acc atc ggc gct ggc ttc att ggt ggt        1296
Val Gly Gly Ala Ile Ser Val Thr Ile Gly Ala Gly Phe Ile Gly Gly
            420                 425                 430 ctg gtt acc ggt atc ttg gct ggt ctc att gcc ctg tgg att ggc tcc        1344
Leu Val Thr Gly Ile Leu Ala Gly Leu Ile Ala Leu Trp Ile Gly Ser
                435                 440                 445 tgg aag gtg cca cgc gtg gtg cag tca ctg atg cct gtg gtc atc atc        1392
Trp Lys Val Pro Arg Val Val Gln Ser Leu Met Pro Val Val Ile Ile
        450                 455                 460 ccg cta ctt acc tca gtg gtt gtt ggt ctc gtc atg tac ctc ctg ctg        1440
Pro Leu Leu Thr Ser Val Val Val Gly Leu Val Met Tyr Leu Leu Leu
465                 470                 475                 480 ggt cgc cca ctc gca tcc atc atg act ggt ttg cag gac tgg cta tcg        1488
Gly Arg Pro Leu Ala Ser Ile Met Thr Gly Leu Gln Asp Trp Leu Ser
                485                 490                 495 tca atg tcc gga agc tcc gcc atc ttg ctg ggt atc atc ttg ggc ctc        1536
Ser Met Ser Gly Ser Ser Ala Ile Leu Leu Gly Ile Ile Leu Gly Leu
            500                 505                 510 atg atg tgt ttc gac ctc ggc gga cca gta aac aag gca gcc tac ctc        1584
Met Met Cys Phe Asp Leu Gly Gly Pro Val Asn Lys Ala Ala Tyr Leu
                515                 520                 525 ttt ggt acc gca ggc ctg tct acc ggc gac caa gct tcc atg gaa atc        1632
Phe Gly Thr Ala Gly Leu Ser Thr Gly Asp Gln Ala Ser Met Glu Ile
        530                 535                 540 atg gcc gcg atc atg gca gct ggc atg gtc cca cca atc gcg ttg tcc        1680
Met Ala Ala Ile Met Ala Ala Gly Met Val Pro Pro Ile Ala Leu Ser
545                 550                 555                 560 att gct acc ctg ctg cgc aag aag ctg ttc acc cca gca gag caa gaa        1728
Ile Ala Thr Leu Leu Arg Lys Lys Leu Phe Thr Pro Ala Glu Gln Glu
                565                 570                 575 aac ggc aag tct tcc tgg ctg ctt ggc ctg gca ttc gtc tcc gaa ggt        1776
Asn Gly Lys Ser Ser Trp Leu Leu Gly Leu Ala Phe Val Ser Glu Gly
            580                 585                 590 gcc atc cca ttc gcc gca gct gac cca ttc cgt gtg atc cca gca atg        1824
Ala Ile Pro Phe Ala Ala Ala Asp Pro Phe Arg Val Ile Pro Ala Met
                595                 600                 605 atg gct ggc ggt gca acc act ggt gca atc tcc atg gca ctg ggc gtc        1872
Met Ala Gly Gly Ala Thr Thr Gly Ala Ile Ser Met Ala Leu Gly Val
        610                 615                 620 ggc tct cgg gct cca cac ggc ggt atc ttc gtg gtc tgg gca atc gaa        1920
Gly Ser Arg Ala Pro His Gly Gly Ile Phe Val Val Trp Ala Ile Glu
625                 630                 635                 640 cca tgg tgg ggc tgg ctc atc gca ctt gca gca ggc acc atc gtg tcc        1968
Pro Trp Trp Gly Trp Leu Ile Ala Leu Ala Ala Gly Thr Ile Val Ser
                645                 650                 655 acc atc gtt gtc atc gca ctg aag cag ttc tgg cca aac aag gcc gtc        2016
Thr Ile Val Val Ile Ala Leu Lys Gln Phe Trp Pro Asn Lys Ala Val
            660                 665                 670
```

```
gct gca gaa gtc gcg aag caa gaa gca caa caa gca gct gta aac gca    2064
Ala Ala Glu Val Ala Lys Gln Glu Ala Gln Gln Ala Ala Val Asn Ala
        675                 680                 685 taa                                                                 2067
```

<210> SEQ ID NO 3
<211> LENGTH: 330
<212> TYPE: PRT
<213> ORGANISM: Corynebacterium glutamicum

<400> SEQUENCE: 3

```
Met Ile Ile Thr Phe Thr Pro Asn Pro Ser Ile Asp Ser Thr Leu Ser
1               5                   10                  15

Leu Gly Glu Glu Leu Ser Arg Gly Ser Val Gln Arg Leu Asp Ser Val
            20                  25                  30

Thr Ala Val Ala Gly Gly Lys Gly Ile Asn Val Ala His Ala Val Leu
        35                  40                  45

Leu Ala Gly Phe Glu Thr Leu Ala Val Phe Pro Ala Gly Lys Leu Asp
    50                  55                  60

Pro Phe Val Pro Leu Val Arg Asp Ile Gly Leu Pro Val Glu Thr Val
65                  70                  75                  80

Val Ile Asn Lys Asn Val Arg Thr Asn Thr Val Thr Glu Pro Asp
                85                  90                  95

Gly Thr Thr Thr Lys Leu Asn Gly Pro Gly Ala Pro Leu Ser Glu Gln
            100                 105                 110

Lys Leu Arg Ser Leu Glu Lys Val Leu Ile Asp Ala Leu Arg Pro Glu
        115                 120                 125

Val Thr Trp Val Val Leu Ala Gly Ser Leu Pro Pro Gly Ala Pro Val
    130                 135                 140

Asp Trp Tyr Ala Arg Leu Thr Ala Leu Ile His Ser Ala Arg Pro Asp
145                 150                 155                 160

Val Arg Val Ala Val Asp Thr Ser Asp Lys Pro Leu Met Ala Leu Gly
                165                 170                 175

Glu Ser Leu Asp Thr Pro Gly Ala Ala Pro Asn Leu Ile Lys Pro Asn
            180                 185                 190

Gly Leu Glu Leu Gly Gln Leu Ala Asn Thr Asp Gly Glu Glu Leu Glu
        195                 200                 205

Ala Arg Ala Ala Gln Gly Asp Tyr Asp Ala Ile Ile Ala Ala Ala Asp
    210                 215                 220

Val Leu Val Asn Arg Gly Ile Glu Gln Val Leu Val Thr Leu Gly Ala
225                 230                 235                 240

Ala Gly Ala Val Leu Val Asn Ala Glu Gly Ala Trp Thr Ala Thr Ser
                245                 250                 255

Pro Lys Ile Asp Val Val Ser Thr Val Gly Ala Gly Asp Cys Ala Leu
            260                 265                 270

Ala Gly Phe Val Met Ala Arg Ser Gln Lys Lys Thr Leu Glu Glu Ser
        275                 280                 285

Leu Leu Asn Ala Val Ser Tyr Gly Ser Thr Ala Ala Ser Leu Pro Gly
    290                 295                 300

Thr Thr Ile Pro Arg Pro Asp Gln Leu Ala Thr Ala Gly Ala Thr Val
305                 310                 315                 320

Thr Gln Val Lys Gly Leu Lys Glu Ser Ala
                325                 330
```

<210> SEQ ID NO 4

```
<211> LENGTH: 688
<212> TYPE: PRT
<213> ORGANISM: Corynebacterium glutamicum

<400> SEQUENCE: 4
```

| | | | | | | | | | | | | | | |
|---|---|---|---|---|---|---|---|---|---|---|---|---|---|---|
|Met|Asn|Ser|Val|Asn|Ser|Ser|Leu|Val|Arg|Leu|Asp|Val|Asp|Phe|
|1| | | |5| | | |10| | | |15| | |
|Gly|Asp|Ser|Thr|Thr|Asp|Val|Ile|Asn|Asn|Leu|Ala|Thr|Val|Ile|Phe|
| | | |20| | | |25| | | |30| | | |
|Asp|Ala|Gly|Arg|Ala|Ser|Ser|Asp|Ala|Leu|Ala|Lys|Asp|Ala|Leu|
| | |35| | | |40| | | |45| | | | |
|Asp|Arg|Glu|Ala|Lys|Ser|Gly|Thr|Gly|Val|Pro|Gly|Gln|Val|Ala|Ile|
|50| | | | |55| | | |60| | | | | |
|Pro|His|Cys|Arg|Ser|Glu|Ala|Val|Ser|Val|Pro|Thr|Leu|Gly|Phe|Ala|
|65| | | |70| | | |75| | | |80| | | |
|Arg|Leu|Ser|Lys|Gly|Val|Asp|Phe|Ser|Gly|Pro|Asp|Gly|Asp|Ala|Asn|
| | | | |85| | | |90| | | |95| | | |
|Leu|Val|Phe|Leu|Ile|Ala|Ala|Pro|Ala|Gly|Gly|Lys|Glu|His|Leu|
| | | |100| | | |105| | | |110| | | | |
|Lys|Ile|Leu|Ser|Lys|Leu|Ala|Arg|Ser|Leu|Val|Lys|Lys|Asp|Phe|Ile|
| | |115| | | |120| | | |125| | | | | |
|Lys|Ala|Leu|Gln|Glu|Ala|Thr|Thr|Glu|Gln|Glu|Ile|Val|Asp|Val|Val|
|130| | | | |135| | | |140| | | | | | |
|Asp|Ala|Val|Leu|Asn|Pro|Ala|Pro|Lys|Thr|Thr|Glu|Pro|Ala|Ala|Ala|
|145| | | | |150| | | | |155| | | | |160|
|Pro|Ala|Ala|Ala|Val|Ala|Glu|Ser|Gly|Ala|Ala|Ser|Thr|Ser|Val|
| | | |165| | | |170| | | |175| | | | |
|Thr|Arg|Ile|Val|Ala|Ile|Thr|Ala|Cys|Pro|Thr|Gly|Ile|Ala|His|Thr|
| | |180| | | |185| | | |190| | | | | |
|Tyr|Met|Ala|Ala|Asp|Ser|Leu|Thr|Gln|Asn|Ala|Glu|Gly|Arg|Asp|Asp|
| |195| | | | |200| | | |205| | | | | |
|Val|Glu|Leu|Val|Val|Glu|Thr|Gln|Gly|Ser|Ser|Ala|Val|Thr|Pro|Val|
| |210| | | | |215| | | |220| | | | | |
|Asp|Pro|Lys|Ile|Ile|Glu|Ala|Ala|Asp|Ala|Val|Ile|Phe|Ala|Thr|Asp|
|225| | | | |230| | | | |235| | | | |240|
|Val|Gly|Val|Lys|Asp|Arg|Glu|Arg|Phe|Ala|Gly|Lys|Pro|Val|Ile|Glu|
| | | |245| | | |250| | | |255| | | | |
|Ser|Gly|Val|Lys|Arg|Ala|Ile|Asn|Glu|Pro|Ala|Lys|Met|Ile|Asp|Glu|
| | |260| | | |265| | | |270| | | | | |
|Ala|Ile|Ala|Ala|Ser|Lys|Asn|Pro|Asn|Ala|Arg|Lys|Val|Ser|Gly|Ser|
| |275| | | | |280| | | |285| | | | | |
|Gly|Val|Ala|Ala|Ser|Ala|Glu|Thr|Thr|Gly|Glu|Lys|Leu|Gly|Trp|Gly|
| |290| | | | |295| | | |300| | | | | |
|Lys|Arg|Ile|Gln|Gln|Ala|Val|Met|Thr|Gly|Val|Ser|Tyr|Met|Val|Pro|
|305| | | | |310| | | | |315| | | | |320|
|Phe|Val|Ala|Ala|Gly|Gly|Leu|Leu|Leu|Ala|Leu|Gly|Phe|Ala|Phe|Gly|
| | | |325| | | |330| | | |335| | | | |
|Gly|Tyr|Asp|Met|Ala|Asn|Gly|Trp|Gln|Ala|Ile|Ala|Thr|Gln|Phe|Ser|
| | |340| | | |345| | | |350| | | | | |
|Leu|Thr|Asn|Leu|Pro|Gly|Asn|Thr|Val|Asp|Val|Asp|Gly|Val|Ala|Met|
| | |355| | | |360| | | |365| | | | | |
|Thr|Phe|Glu|Arg|Ser|Gly|Phe|Leu|Leu|Tyr|Phe|Gly|Ala|Val|Leu|Phe|
| |370| | | | |375| | | |380| | | | | |
|Ala|Thr|Gly|Gln|Ala|Ala|Met|Gly|Phe|Ile|Val|Ala|Ala|Leu|Ser|Gly|

-continued

```
                385                 390                 395                 400
        Tyr Thr Ala Tyr Ala Leu Ala Gly Arg Pro Gly Ile Ala Pro Gly Phe
                            405                 410                 415
        Val Gly Gly Ala Ile Ser Val Thr Ile Gly Ala Gly Phe Ile Gly Gly
                            420                 425                 430
        Leu Val Thr Gly Ile Leu Ala Gly Leu Ile Ala Leu Trp Ile Gly Ser
                            435                 440                 445
        Trp Lys Val Pro Arg Val Val Gln Ser Leu Met Pro Val Val Ile Ile
                    450                 455                 460
        Pro Leu Leu Thr Ser Val Val Gly Leu Val Met Tyr Leu Leu Leu
        465                 470                 475                 480
        Gly Arg Pro Leu Ala Ser Ile Met Thr Gly Leu Gln Asp Trp Leu Ser
                            485                 490                 495
        Ser Met Ser Gly Ser Ser Ala Ile Leu Leu Gly Ile Ile Leu Gly Leu
                            500                 505                 510
        Met Met Cys Phe Asp Leu Gly Gly Pro Val Asn Lys Ala Ala Tyr Leu
                    515                 520                 525
        Phe Gly Thr Ala Gly Leu Ser Thr Gly Asp Gln Ala Ser Met Glu Ile
                    530                 535                 540
        Met Ala Ala Ile Met Ala Ala Gly Met Val Pro Pro Ile Ala Leu Ser
        545                 550                 555                 560
        Ile Ala Thr Leu Leu Arg Lys Lys Leu Phe Thr Pro Ala Glu Gln Glu
                            565                 570                 575
        Asn Gly Lys Ser Ser Trp Leu Leu Gly Leu Ala Phe Val Ser Glu Gly
                    580                 585                 590
        Ala Ile Pro Phe Ala Ala Ala Asp Pro Phe Arg Val Ile Pro Ala Met
                    595                 600                 605
        Met Ala Gly Gly Ala Thr Thr Gly Ala Ile Ser Met Ala Leu Gly Val
                    610                 615                 620
        Gly Ser Arg Ala Pro His Gly Gly Ile Phe Val Val Trp Ala Ile Glu
        625                 630                 635                 640
        Pro Trp Trp Gly Trp Leu Ile Ala Leu Ala Ala Gly Thr Ile Val Ser
                            645                 650                 655
        Thr Ile Val Val Ile Ala Leu Lys Gln Phe Trp Pro Asn Lys Ala Val
                    660                 665                 670
        Ala Ala Glu Val Ala Lys Gln Glu Ala Gln Gln Ala Ala Val Asn Ala
                    675                 680                 685

<210> SEQ ID NO 5
<211> LENGTH: 41
<212> TYPE: DNA
<213> ORGANISM: Artificial
<220> FEATURE:
<223> OTHER INFORMATION: Synthetic DNA

<400> SEQUENCE: 5
atgcgccctg cagggcttct ttactggcac caactggtgc g        41

<210> SEQ ID NO 6
<211> LENGTH: 30
<212> TYPE: DNA
<213> ORGANISM: Artificial
<220> FEATURE:
<223> OTHER INFORMATION: Synthetic DNA

<400> SEQUENCE: 6
ggtaacccca tgacataatc ggaccttgac                    30
```

```
<210> SEQ ID NO 7
<211> LENGTH: 30
<212> TYPE: DNA
<213> ORGANISM: Artificial
<220> FEATURE:
<223> OTHER INFORMATION: Synthetic DNA

<400> SEQUENCE: 7
gtcaaggtcc gattatgtca tggggttacc                                    30

<210> SEQ ID NO 8
<211> LENGTH: 42
<212> TYPE: DNA
<213> ORGANISM: Artificial
<220> FEATURE:
<223> OTHER INFORMATION: Synthetic DNA

<400> SEQUENCE: 8
atatgccctg cagcagggct gtagcaacct gcctcaaagc cg                      42

<210> SEQ ID NO 9
<211> LENGTH: 30
<212> TYPE: DNA
<213> ORGANISM: Artificial
<220> FEATURE:
<223> OTHER INFORMATION: Synthetic DNA

<400> SEQUENCE: 9
gattgaaaga atcagcatga cataatcgga                                    30

<210> SEQ ID NO 10
<211> LENGTH: 30
<212> TYPE: DNA
<213> ORGANISM: Artificial
<220> FEATURE:
<223> OTHER INFORMATION: Synthetic DNA

<400> SEQUENCE: 10
gtcaaggtcc gattatgtca tgctgattct                                    30
```